United States Patent
Peter et al.

[11] 3,943,120
[45] Mar. 9, 1976

[54] SUCCINIMIDO AZO DYESTUFFS

[75] Inventors: Richard Peter; Hans-Joerg Angliker, both of Basel, Switzerland

[73] Assignee: Ciba-Geigy AG, Basel, Switzerland

[22] Filed: Feb. 4, 1974

[21] Appl. No.: 439,651

Related U.S. Application Data

[63] Continuation of Ser. No. 127,366, March 23, 1971, which is a continuation-in-part of Ser. No. 760,081, Sept. 18, 1968, abandoned.

[30] Foreign Application Priority Data

Sept. 19, 1967 Switzerland.................... 13159/67

[52] U.S. Cl. .............. 260/152; 260/156; 260/157; 260/158; 260/239.3 R; 260/247.1 H; 260/268 C; 260/293.88; 260/326 R; 260/490
[51] Int. Cl.² C09B 29/08; C09B 29/36; D06P 3/58; D06P 3/60
[58] Field of Search ........... 260/152, 155, 156, 157, 260/158

[56] References Cited
UNITED STATES PATENTS

| | | |
|---|---|---|
| 2,804,455 | 8/1957 | Dorlars et al. .................. 260/146 R |
| 3,148,178 | 9/1964 | Wallace et al. ..................... 260/152 |
| 3,525,733 | 8/1970 | Weaver et al. ..................... 260/152 |
| 3,624,067 | 11/1971 | Weaver et al. ..................... 260/152 |
| 3,666,746 | 5/1972 | Stanley et al. ..................... 260/152 |

*Primary Examiner*—Floyd D. Higel
*Attorney, Agent, or Firm*—Joseph G. Kolodny; Edward McC. Roberts; Prabodh I. Almaula

[57] ABSTRACT

The invention relates to water-insoluble azo dyestuffs of the formula

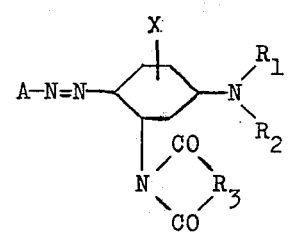

in which A represents the residue of a diazo component of the azobenzene series, $R_1$ a hydrogen atom or an alkyl group which may be substituted which may be substituted, $R_2$ an alkyl group which may be substituted, $R_3$ represents a divalent organic residue which together with the grouping

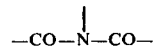

may form a 5- to 7-membered heterocycle, and X represents a hydrogen atom or an alkyl, alkoxy, aryloxy or arylmercapto group. The dyestuffs dye polyester fibre in orange, red or blue shades with good fastness: the use of such succinimido containing azo dyestuffs in imparting blue to red color to fibers or fabrics of wool, cellulose triacetate, polyamides and polyesters. The dyeings display excellent fastness to light, sublimation and abrasion on polyester fibers.

10 Claims, No Drawings

SUCCINIMIDO AZO DYESTUFFS

CROSS-REFERENCE TO RELATED APPLICATION

This is a continuation of application Ser. No. 127,366, filed on Mar. 23, 1971, which in turn is a continuation-in-part of U.S. application Ser. No. 760,081, filed Sept. 16, 1968 (now abandoned).

The present invention is based on the observation that valuable new monoazo dyestuffs of the formula

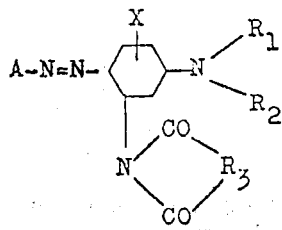

in which A represents the residue of a diazo component, $R_1$ a hydrogen atom or an alkyl group, which may be substituted, $R_2$ an alkyl group which may be substituted, $R_3$ a divalent organic residue which together with the grouping

may form a 5- to 7-membered heterocycle and X represents a hydrogen atom, an alkyl, alkoxy, aryloxy or arylmercapto group, may be obtained when a diazo compound of an aromatic or heterocyclic amine is coupled with a coupling component of the formula

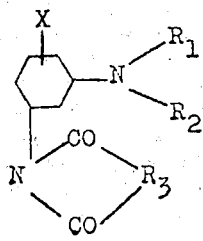

in which X, $R_1$, $R_2$ and $R_3$ have the meanings defined above.

The residue X is preferably a hydrogen atom, a methyl, ethyl, methoxy, ethoxy, phenyloxy or phenylmercapto group.

The groups $R_1$ and $R_2$ may be lower alkyl groups, that is to say they may contain 1 to 4, preferably 2 to 4 carbon atoms, for example methyl, ethyl, n-propyl or n-butyl groups, which may be substituted in the usual manner, for example, by benzyl- or phenylethyl groups, halogenated alkyl groups for example β-chloroethyl, β, β, β-trifluoroethyl or β, γ-dichloropropyl; γ-chloro-β-hydroxypropyl; or by the following groups: β-cyanoethyl; alkoxyalkyl containing up to 8 carbon atoms for example β-ethoxyethyl, δ-methoxybutyl or δ-butoxybutyl; hydroxyalkyl for example β-hydroxyethyl, β, γ-dihydroxypropyl; phenylalkyl containing up to 8 carbon atoms, for example benzyl or phenethyl alkoxy carbonylalkyl containing up to 8 carbon atoms, for example butoxycarbonylethyl, propoxycarbonylethyl, methoxycarbonylpropyl, alkanoylaminoalkyl containing up to 10 carbon atoms, for example β-(acetyl or formyl)-aminoethyl, butyrylaminopropyl; alkanoyloxyalkye containing up to 10 carbon atoms, for example β-acetylhydroxyethyl, β, γ-diacetoxypropyl; butyryloxypropyl, hexanoyloxypropyl; β-aryloxy-sulphonylalkyl for example β-benzenesulphonyloxyethyl or β-(p-chlorobenzenesulphonyl)-ethyl; alkyl- or arylcarbamoylhydroxyalkyl containing up to 7 carbon atoms for example 2-methylcarbamyloxyethyl, γ-butylcarbamyloxypropyl and β-phenylcarbamyloxyethyl; alkyloxycarbonyloxyalkyl containing up to 7 carbon atoms, for example β-(methoxy, ethoxy or isopropoxy)-carbonyloxyethyl, γ-acetamidopropyl, β-(p-nitrophenoxy)-ethyl, β-(p-hydroxyphenoxy)-ethyl, cyanoalkoxyalkyl, e.g. cyanethoxyethyl; β-carboxyethyl, β-acetylethyl, β-diethylaminoethyl, β-cyanoacetoxyethyl- and β-benzoyl- or β-(p-alkoxy or phenoxybenzoyl)-oxyethyl.

As a rule, the groups $R_1$ and $R_2$ contain no more than 18 carbon atoms; they are preferably alkyl residues substituted by chloro, hydroxyl, phenyl, alkoxy of 1–4 carbon atoms, cyanoalkoxy, acyloxy or cyano groups.

The residue $R_3$ is an aliphatic, cycloaliphatic, aromatic or heterocyclic residue derived from an at least dibasic carboxylic acid that is free from substituents imparting solubility in water. Suitable acids from which the residue $R_3$ may be derived are, for example:

succinic acid,
methylsuccinic acid,
dichlorosuccinic acid,
maleic acid,
dichloromaleic acid,
glutaric acid,
dodecenylsuccinic acid,
diglycollic acid,
thiodiglycollic acid,
N-methyl-iminoacetic acid,
hexahydrophthalic acid,
tetrahydrophthalic acid,
endomethylene-tetrahydrophthalic acid,
methyl-endomethylene-tetrahydrophthalic acid,
hexachloro-endomethylene-tetrahydrophthalic acid,
ortho-phthalic acid,
4-methylphthalic acid,
4-nitrophthalic acid,
tetrachlorophthalic acid,
tetrabromophthalic acid,
1,8- or 2,3-naphthalene dicarboxylic acid,
2,2'-diphenic acid,
furan-3,4-dicarboxylic acid, pyridine-2,3-dicarboxylic acid,
pyridine-3,4-dicarboxylic acid and
quinoline-2,3-dicarboxylic acid.

Of special value are the dyestuffs of the formula

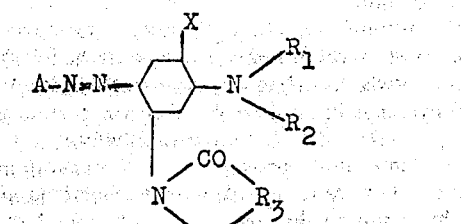

in which X represents a methyl or methoxy group or preferably a hydrogen atom, A represents a substituted benzene residue or a mono- or bicyclic heterocycle, and $R_1$, $R_2$ and $R_3$ have the above meanings.

Of special value are the dyestuffs of the formula

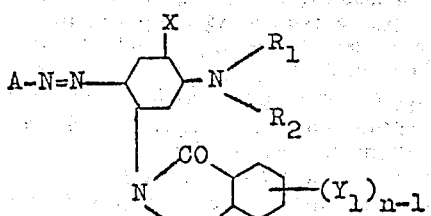

in which $Y_1$ represents a halogen atom, an alkyl, alkoxy, nitro or amino group and n = 1,2 or 3, and the dyestuffs of the formula

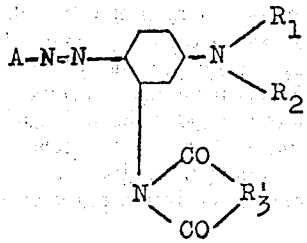

in which $R_3'$ represents a group of the formula —$CH_2$—$X_1$—$CH_2$— (where $X_1$ is a direct bond, a $CH_2$— group, an oxygen or a sulphur atom or an —NH— group, and one or both methylene groups may each carry a substituent, and A, $R_1$ and $R_2$ have the above meanings.

The diazo components to be used according to this invention generally correspond to the formula

A—$NH_2$ wherein A is phenyl optionally substituted by chloro or bromo atoms or by hydroxyl, cyan, thiocyanato, nitro, $C_1$-$C_2$-alkyl (such as methyl or ethyl), trifluoromethyl, $C_1$-$C_2$-alkoxy (such as methoxy or ethoxy), formyl, acetyl, propionyl, benzoxyl, methylbenzoyl, (methyl or ethyl)oxycarbonylbenzoyl, acetylamino, prionylamino, benzoylamino, methoxycarbonylamino, ethoxycarbonylamino, methylsulfonyl, ethylsulfonyl, propylsulfonyl, chloromethylsulfonyl, aminosulfonyl, $C_1$-$C_2$-alkylated aminosulfonyl (such as methylaminosulfonyl, diethylaminosulfonyl), (hydroxyethyl)-aminosulfonyl, cyanoethylaminosulfonyl, β-chloroethylsulfonylamino, cyclohexylaminosulfonyl, phenylaminosulfonyl, (chloro-, methyl-, nitro- or methoxyphenyl)aminosulfonyl, benzylaminosulfonyl, N-piperidylsulfonyl, N-morpholinosulfonyl, $C_1$-$C_3$-alkylsulfonyloxy (such as methylsulfonyloxy, ethylsulfonyloxy, propylsulfonyloxy), ethoxyethylsulfonyloxy, cyclohexylsulfonyloxy, chloromethylsulfonyloxy, cyanethylsulfonyloxy, phenylsulfonyloxy, chlorophenylsulfonyloxy, aminosulfonyloxy, $C_1$-$C_4$-alkylated aminosulfonyloxy (such as ethylaminosulfonyloxy, butylaminosulfonyloxy, dibutylaminosulfonyloxy, diethylaminosulfonyloxy), phenylaminosulfonyloxy, N-phenyl-N-ethyl-aminosulfonyloxy, phenyl, acetylaminophenyl, trimethylammonium, phenoxy, phenylazo or nitrophenylazo groups.

A valuable class of dyestuffs are those wherein the diazo component A is a phenyl residue which contains at least one electro-negative (electron-attracting) substituent. Such substituents are characterized by a positive Hammet-value as defined in British Specification No. 1,098,654, or by Jaffe, Chemical Reviews, Vol 53, page 191 (particularly at pages 219–233), and H.C. Brown et al., J.Am.Chem. Soc., vol. 80, pages 4979–4987 (1958), especially in table No. 1.

Another selection of diazo components to be used according to this invention preferably correspond to the formula

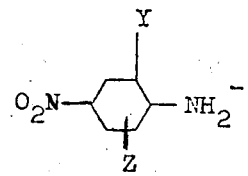

in which Y represents a hydrogen or halogen atom, an alkyl, alkoxy, phenoxy, nitro, cyano, carbalkoxy or alkylsulphonyl group, and Z represents a nitro or cyano group. As examples of relevant diazo compounds the following amines may be mentioned:

1-amino-4-chlorobenzene,
1-amino-4-bromobenzene,
1-amino-4-methylbenzene,
1-amino-4-nitrobenzene,
1-amino-4-cyanobenzene,
1-amino-2,5-dicyanobenzene,
1-amino-4-methylsulphonylbenzene,
1-amino-4-carbomethyoxybenzene,
1-amino-2,4-dichlorobenzene,
1-amino-2,4-dibromobenzene,
1-amino-2-methyl-4-chlorobenzene,
1-amino-2-trifluoromethyl-4-chlorobenzene,
1-amino-2-cyano-4-chlorobenzene,
1-amino-2-carbomethoxy-4-chlorobenzene,
1-amino-2-carbomethoxy-4-nitrobenzene,
1-amino-2-chloro-4-cyanobenzene,
1-amino-2-chloro-4-nitrobenzene,
1-amino-2-phenoxy-4-nitrobenzene,
1-amino-2-chloro-4-carbethoxybenzene,
1-amino-2-chloro-4-methylsulphonylbenzene,
1-amino-2-methylsulphonyl-4-chlorobenzene,
1-amino-2-methylsulphonyl-4-nitrobenzene,
1-amino-2,4-dinitrobenzene,
1-amino-2,4-dicyanobenzene,
1-amino-2-cyano-4-methylsulphonylbenzene,
1-amino-2,6-dichloro-4-cyanobenzene,
1-amino-2,6-dichloro-4-nitrobenzene,
1-amino-2,4-dicyano-6-chlorobenzene,
1-amino-2,4,6-trinitrobenzene,
1-amino-2,4-dinitro-6-chloro- or -bromobenzene, and especially 1-amino-2-cyano-4-nitrobenzene,
4-aminoazobenzene,
4-amino-3-nitro-1,1'-azobenzene,
4-amino-3-nitro-4'-chloro-1,1'-azobenzene,
4-amino-3-nitro-2'-chloro-1,1'-azobenzene,
4-amino-3-nitro-2'-methoxy-1,1'-azobenzene and
4-amino-3-nitro-4'-methyl-1,1'-azobenzene.

From the series of the heterocyclic diazo components the following may be mentioned:

2-aminothiazole,
2-amino-5-nitrothiazole,
2-amino-5-cyanothiazole,
2-amino-4-methyl-5-nitrothiazole,
2-amino-4-methylthiazole,
2-amino-4-phenylthiazole, 2-amino-4-(4'-chloro)-phenylthiazole,
2-amino-4-(4'-nitro)-phenylthiazole,
2-amino-6-chlorobenzthiazole,
2-amino-6-cyanobenzthiazole,
2-amino-6-nitrobenzthiazole,
2-amino-1,3,4-thiadiazole and
2-amino-1,3,5-thiadiazole.

The coupling components to be used according to this invention preferably correspond to the formula

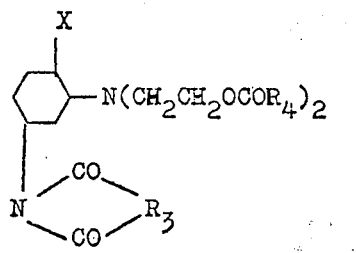

in which $R_4$ represents an alkyl group, for example methyl, ethyl, propyl or butyl, or a heterocyclic residue, for example a furan, tetrahydrofuran, thiophene or tetrahydrothiophene residue and $R_3$ and X have the above meanings. $R_3$ is preferably a residue of the formula

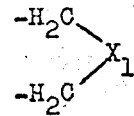

in which $X_1$ represents a direct bond, a $CH_2$-group, an oxygen or a sulphur atom or an —NH— group.

As relevant examples the following compounds may be mentioned:

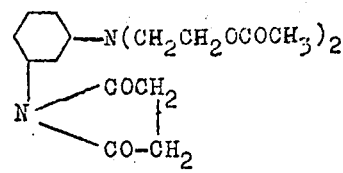 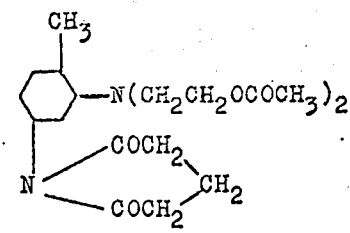

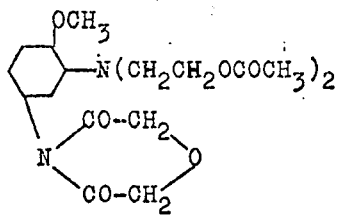 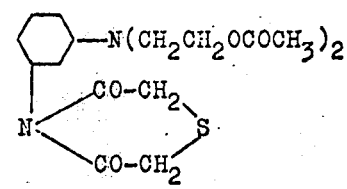

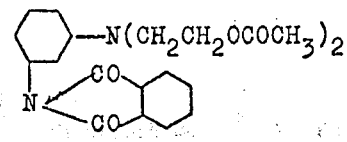 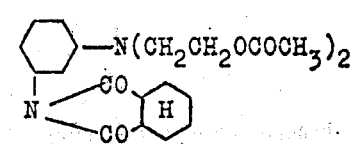

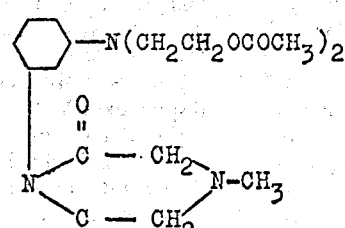 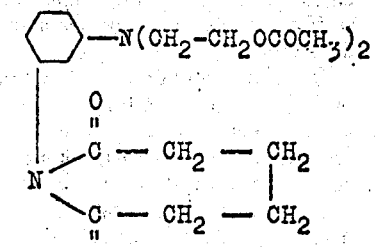

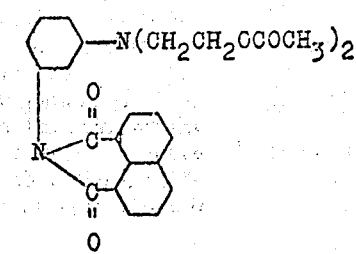

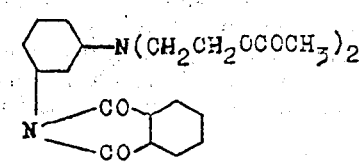
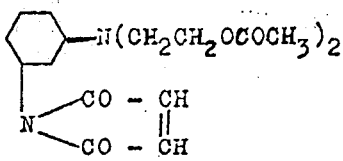

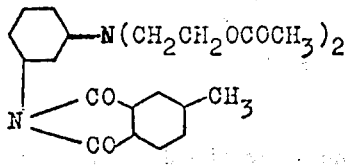
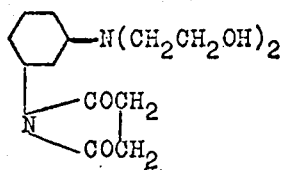

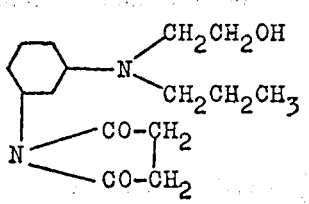
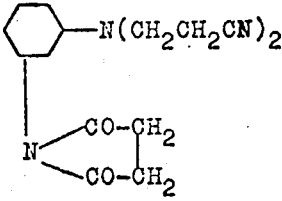

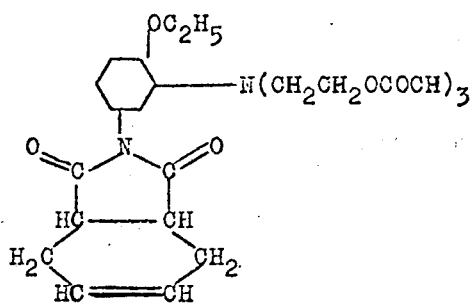

Instead of a simple coupling component a mixture of coupling components may be used, whereby in many cases the affinity and the build-up of the resulting dyestuff mixture is improved compared with the individual dyestuffs.

The afore-mentioned diazo components may be diazotized by known methods, for example with a mineral acid, especially hydrochloric acid, and sodium nitrite or, for example, with a solution of nitrosylsulphuric acid in concentrated sulphuric acid.

Coupling may likewise be carried out in known manner, for example in a neutral to acidic medium, if desired or required in the presence of sodium acetate or similar buffer substances that are capable of influencing the coupling speed, or of catalysts, for example pyridine or a pyridine salt.

On completion of the coupling reaction the dyestuffs formed are easy to separate from the coupling mixture, for example by filtration since they are substantially insoluble in water.

The new dyestuffs are excellently suitable for dyeing or printing materials, especially fibres or fabrics, for instance of cellulose triacetate and polyamides, but especially of aromatic polyesters, on which strong dyeings of excellent fastness properties are obtained, especially fastness to light, sublimation and abrasion. Such dyeings may also be further improved by a premanent-press process, for example by the Koratron process. Dyeing with the new dyestuffs finished in this manner display excellent fastness to wetting and heat.

For dyeing the new dyestuffs are advantageously used in a finely disperse form and with addition of dispersants for example soap, sulphite cellulose waste liquor or synthetic detergents, or a combination of different wetting and dispersing agents. As a rule it is advantageous to convert these dyestuffs into a dye preparation before dyeing; such a preparation contains a dispersant and finely disperse dyestuff in such a form that when the dye preparation is diluted with water a fine dispersion is obtained. Such dyestuff preparations may be manufactured in known manner, for example by reprecipitating the dyestuff from sulphuric acid and grinding the resulting suspension with sulphite cellulose waste liquor, or by grinding the dyestuff in a highly efficient mill in dry or wet form, with or without addition of a dispersant during the grinding operation.

When strong dyeings on polyethylene terephthalate fibres are to be produced it is advantageous to add a swelling agent to the dyebath or preferably to perform the dyeing operation under superatmospheric pressure at a temperature above 100°C, for example at 120°C. Suitable swelling agents are aromatic carboxylic acid, for instance benzoic or salicylic acid, phenols, for example ortho- or para-hydroxydiphenyl, aromatic halogen compounds, for example chlorobenzene, orthodichlorobenzene or trichlorobenzene, phenylmethylcarbinol or diphenyl. When dyeing under superatmospheric pressure it is advantageous to make the dyebath weakly acidic, for example by addition of a weak acid, for instance acetic acid.

By virtue of their alkali fastness the new dyestuffs are also suitable for dyeing by the so-called thermofixing process, according to which the fabric to be dyed is impregnated with an aqueous dispersion of the dyestuff, which advantageously contains 1 to 50% of urea and a thickner, especially sodium alginate, preferably at a temperature not exceeding 60°C, and the fabric is then squeezed in the usual manner, advantageously to a weight increase of 50 to 100% calculated on the weight of the dry fabric.

To fix the dyestuff on the fabric thus impregnated it is dried, for example in a current of warm air, and then heated to a temperature above 100°C, for example from 180° to 220°C.

The thermofixing process just mentioned is of special importance in the dyeing of mixed weaves of polyester fibres and cellulose fibres, especially cotton. In this application the padding liquor contains, in addition to the dyestuffs of this invention, also dyestuffs suitable for dyeing cotton, especially vat dyes, or reactive dyestuffs, that is to say dyestuffs that can be fixed on cellulose fibre with formation of a chemical bond, thus for instance dyestuffs containing a chlorotriazine or chlorodiazine residue. In the latter case it is advantageous to incorporate with the padding solution an acid acceptor, for example an alkali metal carbonate, phosphate, borate or perborate or mixtures thereof. When vat dyes are used the padded fabric must be treated, after the heat treatment, with an aqueous alkaline solution of one of the reducing agents commonly used in vat dyeing.

Since they reserve well on wool the dyestuffs of this invention are also excellently suitable for dyeing mixed weaves of polyester fibres and wool.

The resulting dyeings are advantageously aftertreated, for example heated in an aqueous solution of a nonionic detergent.

The dyestuffs may also be applied by printing instead of by impregnation, for example with the use of a printing ink that contains the finely dispersed dyestuff together with the assistants conventionally used in printing, for example wetting and thickening agents, if desired in admixture with one of the cotton dyestuffs mentioned above with or without urea and/or an acid acceptor.

Unless otherwise indicated, parts and percentages in the following Examples are by weight.

Instruction 1 (Manufacture of the intermediates)

28 Parts of N,N-bis-(β-acetoxyethyl)-3-aminoaniline [prepared according to Swiss Patent Application 12,254/67 -Case 6261] are intimately mixed with 15 parts of phthalic anhydride and while stirring heated for 15 minutes in a bath maintained at 200°C. After cooling, the product is recrystallized from 200 parts by volume of alcohol, suction-filtered, washed with ethanol and then with petroleum ether. After drying 23 parts of a yellowish powder are obtained of the formula

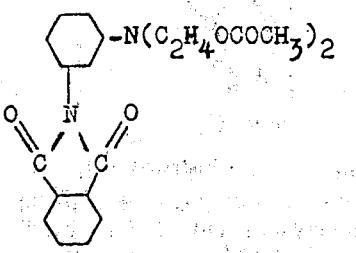

melting at 118° – 119°C. Repeated recrystallization does not change the melting point.

Instruction 2

10.7 Parts of N,N-dicyanoethyl-m-phenylenediamine [obtained by hydrolyzing N,N-dicyanoethyl-m-acetanilide] and 7.4 parts of phthalic anhydride are stirred for 15 minutes at 200°C, cooled and the product recrystallized from butanol–dioxane, to yield 13.4 parts (=78% of theory) of a compound of the formula

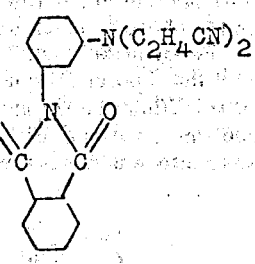

melting at 160° to 162°C.

Instruction 3

A mixture of 8.4 parts of N,N,-diacetoxyethyl-m-phenylenediamine and 3 parts of succinic anhydride in 100 parts of benzene is refluxed for 3 hours and cooled. The white residue is suction-filtered, washed with a small quantity of benzene and dried in a vacuum cabinet at 60° to 70°C, to yield 10.4 parts (=91% of theory) of a product of the formula

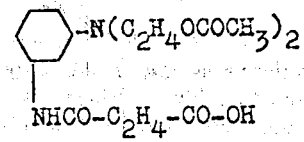

melting at 115°c.

3.8 Parts of this product are suspended in 60 parts of acetic anhydride, 6 parts of anhydrous sodium acetate are added and the whole is refluxed for 3 hours, poured into water, taken up in ethyl acetate and the organic phase is washed neutral. The ethyl acetate is evaporated and the residue recrystallized from butanol, to yield 26.8 parts (=74% of theory) of a beige-coloured powder of the formula

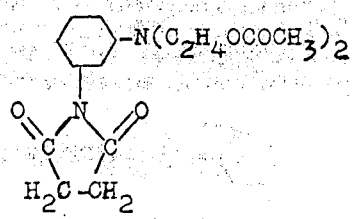

melting at 89 to 91°C.

Instruction 4

A mixture of 6.9 parts of m-nitroaniline, 5 parts of succinic anhydride and 30 parts of o-dichlorobenzene is refluxed overnight, cooled with stirring, and the product of the formula

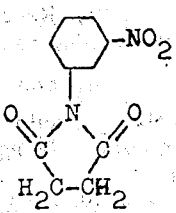

is suction-filtered, washed with benzene and petroleum ether and dried at 70°C, to leave 10 parts (= 91.8% of theory) of a product melting at 168° to 171°C.

400 Parts of the above product are hydrogenated in the presence of Raney nickel in 600 parts of dimethylformamide until the theoretical quantity of hydrogen has been absorbed. While still hot the catalyst is filtered and the residue washed with dimethylformamide. The filtrate is poured into water, whereupon the amine of the formula

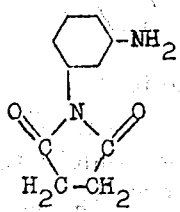

settles out; it is suction-filtered and thoroughly washed with water and dried, to yield 300 parts of a beigecoloured powder melting at 191° to 193°C. This amine may be substituted at the nitrogen atom in the usual manner, for example by treating with acrylonitrile or ethylene oxide.

Instruction 5

The procedure is as described in instruction 3 except that succinic anhydride is replaced by 2.9 parts of maleic anhydride; yield: 9.8 parts (=86.8% of theory) of a product of the formula

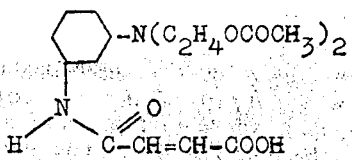

When 3.8 parts of this product are cyclized with the aid of sodium acetate in acetic anhydride as described in instruction 3, 3.5 parts of a product are obtained of the formula

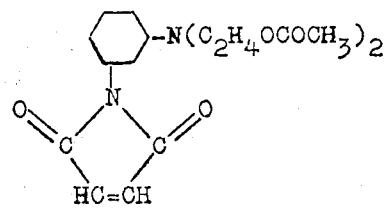

EXAMPLE 1

A mixture of 1.73 parts of 2-chloro-4-nitroaniline, 20 parts of water and 3 parts by volume of concentrated hydrochloric acid is stirred, cooled to 0°C and diazotized with 6 parts by volume of 2N sodium nitrite solution, stirred for one hour and then filtered. The excess nitrite is decomposed with sulphamic acid.

The resulting solution is dropped at 0° to 10°C into a solution of 4.1 parts of the product of Instruction 1 in 150 parts of dimethylformamide, the whole is stirred overnight at 0° to 10°C; the dyestuff is completely precipitated with ice water, filtered, washed neutral and dried under vacuum. The resulting dyestuff of the formula

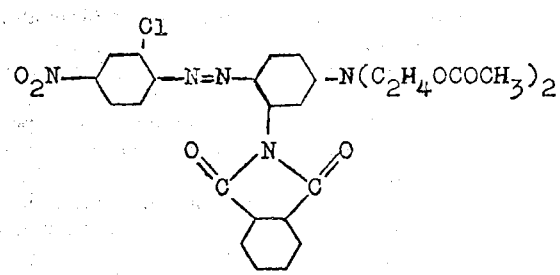

dyes polyester fast scarlet tints.

EXAMPLE 2

3.5 Parts of 2-cyano-4-nitroaniline are diazotized with 21 parts by volume of N-nitrosylsulphuric acid, poured into 250 parts of ice-water and the solution is clarified by filtration. While stirring at 0° to 5°C, the filtrate is added to a solution of 8.2 parts of the product of Instruction 1 in 600 parts of acetone and 50 parts of water and the whole is stirred for 3 hours at 0° to 5°C. The resulting dyestuff of the formula

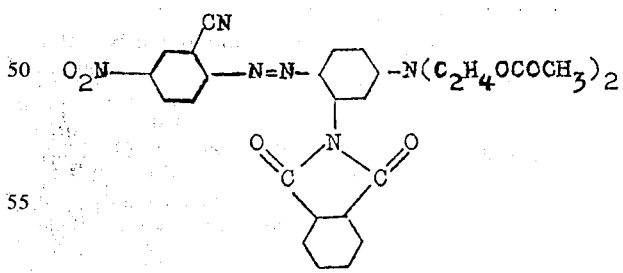

is suction-filtered and thoroughly washed with water. It can be recrystallized from acetone and produces on polyester material bluish red tints which are extremely fast to light and sublimation.

EXAMPLE 3

1.63 Parts of 2-cyano-4-nitroaniline are diazotized with 10 parts by volume of N nitrosylsulphuric acid, poured into ice-water and the excess nitrite is decomposed with sulphanil acid. While stirring at 0° to 5°C, this solution is mixed dropwise with a solution of 3.6 parts of the product of Instruction 5 in 30 parts by volume of 80% acetic acid. After 30 minutes the batch is diluted with 1000 parts by volume of ice-water and then stirred for another 2 hours. The precipitate is suction-filtered, thoroughly washed with water and dried under vacuum, to yield 4.6 parts of the dyestuff of the formula

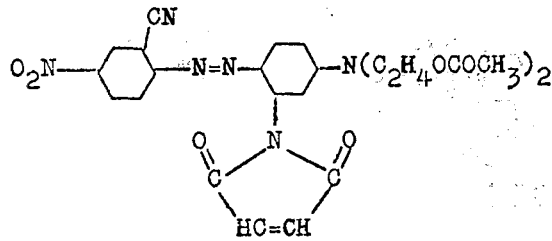

which dyes polyester material fast bluish red shades.

The following Table lists further components from which dyestuffs may be obtained when the diazo component of column I is diazotized and coupled with the coupling component of column II. The tints produced on polyester material with these dyestuffs are shown in column III.

| | I | II | III |
|---|---|---|---|
| 1 | 4-nitroaniline | ![structure] | orange |
| 2 | 2-cyano-4-nitro-aniline | ![structure] | bluish red |
| 3 | 4-nitroaniline | " | orange |
| 4 | 2,6-dichloro-4-nitroaniline | " | brown orange |
| 5 | 2-chloro-4-nitro-aniline | | red |
| 6 | 2-chloro-4-methyl-sulphonylaniline | ![structure] | orange |
| 7 | 4-nitro-anthranilic acid methyl ester | " | red |
| 8 | 6-ethoxy-2-amino-benzthiazole | " | red |
| 9 | 2-cyano-4-Nitro-aniline | ![structure] | red |
| 10 | 2-chloro-4-nitro-aniline | " | orange |
| 11 | 4-nitroaniline | ![structure] | red |

-continued

| I | | II | III |
|---|---|---|---|
| 12 | 2-cyano-4-nitro-aniline | cyclohexane with OCH₃, NHC₂H₄CN, and N-linked maleimide (HC=CH) substituents | bluish |
| 13 | 2-chloro-4-nitro-aniline | cyclohexane with N(C₂H₄CN)(C₂H₄OH) and N-linked succinimide (H₂C–CH₂) | red |
| 14 | 4-nitroaniline | cyclohexane with N(C₂H₄CN)(C₂H₄OCOCH₃) and N-linked succinimide | orange |
| 15 | 4-nitroaniline | cyclohexane with N(C₂H₄OCOCH₃)₂ and N-linked imide with H₂C–O–CH₂ bridge | orange |
| 16 | 4-nitroaniline | cyclohexane with N(C₂H₄OCOCH₃)₂ and N-linked imide with H₂C–S–CH₂ bridge | orange |
| 17 | 2-chloro-4-nitro-aniline | cyclohexane with N(C₂H₄OCOCH₃)₂ and N-linked bicyclic imide | red |

-continued

| I | | II | III |
|---|---|---|---|
| 18 | 2-cyano-4-nitro-aniline | 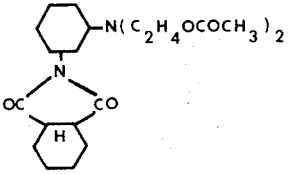 | bluish red |
| 19 | 2,6-dichloro-4-nitro-aniline | " | brown orange |
| 20 | 2-cyano-4-nitro-aniline | 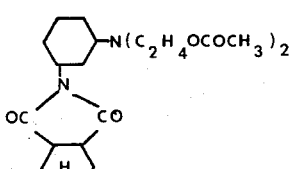 | bluish red |
| 21 | 2-chloro-4-nitro-aniline | " | red |
| 22 | 2,6-dichloro-4-nitro-aniline | " | brown orange |
| 23 | 2,4-dinitro-6-chloro-aniline | 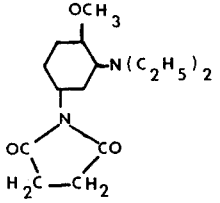 | blue |

EXAMPLE 4

High-temperature Dyeing

1 Part of the dyestuff obtained in Example 1 is ground in the wet state with 2 parts of a 50% aqueous solution of the sodium salt of 1,1'-dinaphthylmethane-2, 2'-disulphonic acid and then dried.

This dyestuff preparation is stirred with 40 parts of a 10% aqueous solution of the sodium salt of N-benzyly-heptadecyl-benzimidazole disulphonic acid, and 4 parts of a 40% acetic acid solution are added. By dilution of this mixture with water a dyebath of 4000 parts is prepared.

100 Parts of a cleaned polyester fibre fabric are entered in this dyebath at 50°C; the temperature is then raised within half an hour to 120° to 130°C and dyeing is carried out for 1 hour at this temperature in a closed vessel and then thoroughly rinsed. A strong scarlet dyeing of excellent fastness to light and sublimation is obtained.

EXAMPLE 5

Continuous dyeing process

20 Parts of the dyestuff of Example 2 are mixed with a solution of 40 parts of sodium dinaphthylmethane disulphonate in 140 parts of water and ground.

A padding liquor is prepared containing 200 parts of the above dyestuff preparation, 100 parts of carboxymethylcellulose (4% aqueous solution) and 700 parts of water by stirring the dyestuff preparation described above into the previously diluted thickener by means of a high-speed stirrer, and the mixture is then adjusted to a pH value of 6 by means of 80% acetic acid. A polyester fabric is then padded in this solution at 30°C and squeezed to a weight increase of 60% and then dried at 70° to 80°C. The fabric is then placed on a tenter and heated for 60 seconds at about 210°C, then washed in hot water and thoroughly rinsed in cold water. The fabric thus treated displays a bluish red shade having good fastness properties.

EXAMPLE 6

A mixed weave of 33% cotton and 67% polyethylene terephthalate fibres is first dyed as described in Example 4 with the dyestuff obtained in Example 1 to colour the polyester part. The cotton part is then dyed in the usual manner with a water-soluble reactive dyestuff. The fabric is then dried.

The dyed mixed fabric is padded at 30°C with a resin-containing bath and squeezed to a weight increase of 50% (that is to say 12.5% of resin referred to the weight of the fibre), dried for 2 minutes at 93°C and simultaneously fixed and shaped in an oven in which air circulates. A permanently shaped fabric is obtained. The dyestuff absorbed on the polyester part does not sublime during the curing of the resin former.

The resinous padding liquor contains per litre: 250 g of glyoxal-monourein (called "resin" for short), 20 g of a polyethylene softener (marketed by Sun Chemical under the trade name Mykon SF), 1 g of a nonionic wetting agent (marketed by Sun Chemical under the trade name Mykon WA) and 45 g of a zinc nitrate preparation (marketed by Sun Chemical under the trade name Catalyst X-4). To prepare the liquor the wetting agent is dissolved in 10 times its own weight of water heated at about 30°C, and the solution is added to the bath and mixed. The resin is then stirred in and finally the polyethylene softener is stirred into the mixture. The zinc nitrate preparation is only added immediately before the padding operation.

We claim:

1. A water-insoluble azo dyestuff of the formula

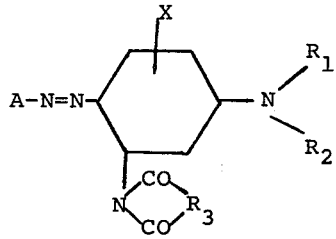

in which A represents phenyl or phenyl substituted by chloro, bromo, hydroxyl, cyan, thiocyanato, nitro, alkyl of 1 to 2 carbon atoms, trifluoromethyl, alkoxy of 1 to 2 carbon atoms, formyl, acetyl, propionyl, benzoyl, methylbenzoyl, (methyl or ethyl) oxycarbonylbenzoyl, acetylamino, propionylamino, benzoylamino, methoxycarbonylamino, ethoxycarbonylamino, methylsulfonyl, ethylsulfonyl, propylsulfonyl, chloromethylsulfonyl, aminosulfonyl, alkylated aminosulfonyl containing 1 to 2 carbon atoms, (hydroxyethyl)-aminosulfonyl, cyanoethylaminosulfonyl, β-chloroethylsulfonylamino, cyclohexylaminosulfonyl, phenylaminosulfonyl, (chloro-, methyl-, nitro- or methoxy-phenyl) aminosulfonyl, benzylaminosulfonyl, N-piperidylsulfonyl, N-morpholinosulfonyl, alkylsulfonyloxy containing 1 to 3 carbon atoms, ethoxyethylsulfonyloxy, cyclohexylsulfonyloxy, chloromethylsulfonyloxy, cyanethylsulfonyloxy, phenylsulfonyloxy, chlorophenylsulfonyloxy, aminosulfonyloxy, alkylaminosulfonyloxy containing 1 to 4 carbon atoms, phenylaminosulfonyloxy, N-phenyl-N-ethyl-aminosulfonyloxy, phenyl, acetylaminophenyl, trimethylammonium, phenoxy, phenylazo or nitrophenylazo, $R_1$ is hydrogen, alkyl containing 1 to 10 carbon atoms or alkyl containing 1 to 10 carbon atoms substituted by a member selected from the group consisting of chlorine, bromine, phenyl, alkanoyloxy of 1 to 10 carbon atoms, alkanoylamino of 1 to 10 carbon atoms, hydroxy, cyano, alkoxy of 1 to 4 carbon atoms, benzoyl, cyanethoxy, alkylcarbamoyl where the alkyl contains 2 to 7 carbon atoms, aminocarbonyl and alkyloxycarbonyloxy in which alkyl contains 2 to 7 carbon atoms, $R_2$ is alkyl containing 1 to 10 carbon atoms or alkyl containing 1 to 10 carbon atoms substituted by a member selected from the group consisting of chlorine, bromine, phenyl, alkanoyloxy of 1 to 10 carbon atoms, hydroxy, cyano, alkylcarbamoyl in which alkyl contains 2 to 7 carbon atoms, aminocarbonyl and alkyloxycarbonyloxy in which alkyl contains 2 to 7 carbon atoms, alkoxy of 1–4 carbon atoms, benzoyl and cyanethoxy, $R_3$ represents —CH$_2$—X$_1$—CH$_2$— wherein X$_1$ is a direct bond, a double bond, —CH$_2$—, —O—, —S—, —NH—, —N(CH$_3$)—, or

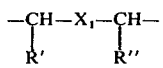

where R' and R'' are hydrogen or a group as defined below and where one or both of R' and R'' is chlorine, an alkyl radical of between 1 to 12 carbon atoms,

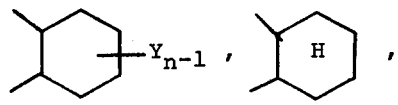

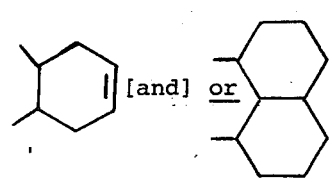

wherein Y is chlorine, alkyl of 1 to 3 carbon atoms, alkoxy of 1 to 3 carbon atoms, nitro or NH$_2$ and $n = 1$, 2 or 3, and X represents hydrogen, alkyl of up to 3 carbon atoms, alkoxy of up to two carbon atoms, phenoxy or phenylmercapto.

2. A dyestuff as claimed in claim 1 of the formula

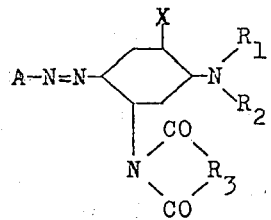

where X, A, $R_1$, $R_2$ and $R_3$ have the same meanings as in claim 1.

3. A dyestuff as claimed in claim 2, in which the residue $R_3$ is —CH$_2$—X$_1$—CH$_2$— where X$_1$ is a direct bond, —CH$_2$—, oxygen, sulfur or —NH—, or

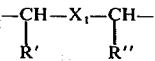

where X$_1$ is a direct bond, —CH$_2$—, oxygen, sulfur or —NH— and one or both of R' and R'' is chlorine or alkyl of 1 to 12 carbon atoms.

4. A dyestuff as claimed in claim 3 in which X$_1$ is a direct bond or —CH$_2$—.

5. A dyestuff as claimed in claim 2, in which the residue $R_3$ is

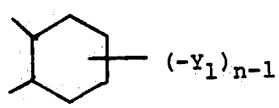
and $Y_1$ is chlorine, alkyl of 1 to 3 carbon atoms, alkoxy of 1 to 3 carbon atoms, nitro or $NH_2$ and $n$ is 1, 2 or 3.
6. A dyestuff according to claim 2 of the formula
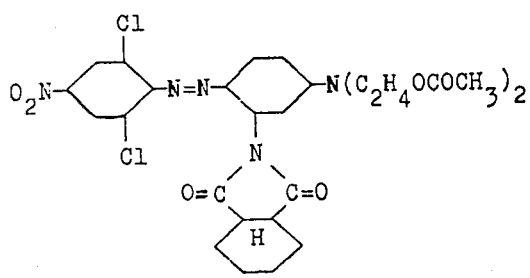
7. A dyestuff according to claim 5 of the formula
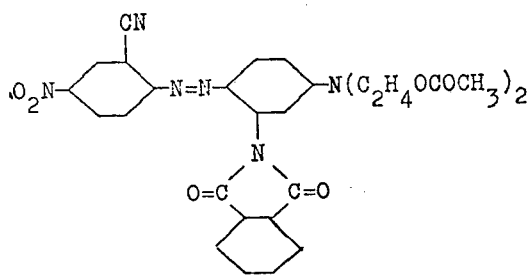
8. A dyestuff according to claim 4 of the formula
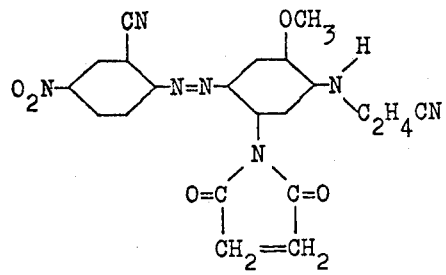
9. A dyestuff according to claim 2 of the formula
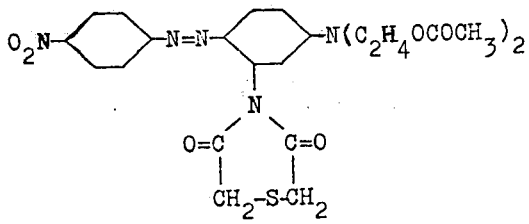
10. A dyestuff according to claim 3 of the formula
* * * * *

UNITED STATES PATENT AND TRADEMARK OFFICE
CERTIFICATE OF CORRECTION

PATENT NO. : 3,943,120
DATED : March 9, 1976
INVENTOR(S) : RICHARD PETER ET AL.

It is certified that error appears in the above-identified patent and that said Letters Patent are hereby corrected as shown below:

In column 20, line 30, the structural formula, replace "[and] or" by -- or --.

Signed and Sealed this eleventh Day of May 1976

[SEAL]

Attest:

RUTH C. MASON
Attesting Officer

C. MARSHALL DANN
Commissioner of Patents and Trademarks